US008105475B2

(12) United States Patent  (10) Patent No.: US 8,105,475 B2
Tixier et al.  (45) Date of Patent: Jan. 31, 2012

(54) APPARATUS AND METHOD FOR DETERMINING THE COMPOSITION OF A MATERIAL BEING EXAMINED

(75) Inventors: Sébastien Tixier, North Vancouver (CA); Dan Bizzotto, North Vancouver (CA)

(73) Assignee: Honeywell International Inc., Morristown, NJ (US)

( * ) Notice: Subject to any disclaimer, the term of this patent is extended or adjusted under 35 U.S.C. 154(b) by 961 days.

(21) Appl. No.: 12/102,159

(22) Filed: Apr. 14, 2008

(65) Prior Publication Data

US 2009/0255829 A1  Oct. 15, 2009

(51) Int. Cl.
 *G01N 27/26* (2006.01)
 *G01N 27/416* (2006.01)
(52) U.S. Cl. ............. 205/775; 205/793.5; 204/406; 204/400; 162/263; 162/252; 702/116
(58) Field of Classification Search .......... 204/400–435; 205/775–794.5
See application file for complete search history.

(56) References Cited

U.S. PATENT DOCUMENTS

| 5,822,220 | A | 10/1998 | Baimes |
| 6,235,123 | B1 | 5/2001 | Millar |
| 6,416,651 | B1 | 7/2002 | Millar |
| 7,290,450 | B2 | 11/2007 | Brown et al. |

OTHER PUBLICATIONS

"Electrode" U.S. Appl. No. 11/903,644, filed Sep. 24, 2007.

*Primary Examiner* — Jeffrey T Barton
*Assistant Examiner* — Jennifer Dieterle (57) ABSTRACT

A method includes identifying first data associated with cyclic voltammetry measurements of a material being examined. The cyclic voltammetry measurements include applying a varying first voltage to the material and measuring a first current. The method also includes identifying second data associated with impedance measurements. The impedance measurements include applying a second voltage to the material and measuring a second current. The second data includes a scaling factor. The method further includes adjusting at least part of the first data using the scaling factor and identifying a composition of the material using the adjusted first data. The first data could include a current versus voltage curve that associates values of the first current to values of a sweep voltage. The first data could be adjusted by normalizing the curve using the scaling factor, and the normalized curve could be used to generate a current derivative curve.

20 Claims, 3 Drawing Sheets

APPARATUS AND METHOD FOR DETERMINING THE COMPOSITION OF A MATERIAL BEING EXAMINED

TECHNICAL FIELD

This disclosure relates generally to measurement systems and more specifically to an apparatus and method for determining the composition of a material being examined.

BACKGROUND

Various industrial processes routinely use liquid and other materials for a wide variety of purposes. It is often necessary or desirable to monitor the composition of the materials in order to accurately control the processes being performed. For example, a wood pulping process typically uses chemicals to produce wood pulp from wood chips. One example of a wood pulping process is a kraft wood pulping process, which is considered "circular" since chemicals used during the process are recovered and reused again in the process. To control the quality of the wood pulp being produced in the kraft wood pulping process, sensors can be used to measure characteristics of the chemicals being recycled.

The kraft wood pulping process and other processes routinely include harsh and hostile environments. Contaminants and scale can therefore quickly form on electrodes in the sensors used in these processes. This leads to measurement drift and a loss of measurement accuracy. As a result, these processes often cannot be controlled as accurately as possible, which can lead to process inefficiencies and monetary losses.

SUMMARY

This disclosure provides an apparatus and method for determining the composition of a material being examined.

In a first embodiment, a method includes identifying first data associated with cyclic voltammetry measurements of a material being examined. The cyclic voltammetry measurements include applying a varying first voltage to the material and measuring a first current generated using the varying first voltage. The method also includes identifying second data associated with impedance measurements. The impedance measurements include applying a second voltage to the material and measuring a second current generated using the second voltage. The second data includes a scaling factor. The method further includes adjusting at least part of the first data using the scaling factor and identifying a composition of the material using the adjusted first data.

In particular embodiments, identifying the first data includes applying a sweep voltage to the material being examined and measuring the first current. The sweep voltage varies over a range of voltages, and the first current is based on the sweep voltage. Also, identifying the first data includes generating a current versus voltage curve that associates values of the first current to values of the sweep voltage.

In other particular embodiments, identifying the second data includes applying a sinusoidal voltage to the material being examined and measuring the second current. The sinusoidal voltage is applied at multiple frequencies, and the second current is based on the sinusoidal voltage. Also, identifying the second data includes generating the scaling factor using measurements of the second current.

In yet other particular embodiments, adjusting at least part of the first data includes normalizing the current versus voltage curve using the scaling factor to produce a normalized current versus voltage curve. Also, the method could further include generating a current derivative curve using the normalized current versus voltage curve. The current derivative curve associates changes in the first current against changes in the sweep voltage as identified in the normalized current versus voltage curve. The current derivative curve could be used to identify the composition of the material.

In still other particular embodiments, identifying the second data includes identifying a conductivity of the material being examined. Also, identifying the composition of the material includes using the identified conductivity of the material.

In other particular embodiments, the cyclic voltammetry measurements include applying the first voltage across first and second electrodes of a sensor probe during multiple cycles. Also, the method further includes swapping the second electrode and a third electrode during the multiple cycles of the cyclic voltammetry measurements.

In additional particular embodiments, the second voltage is applied at multiple frequencies and has a magnitude substantially less than the varying first voltage. For example, the first voltage could have a maximum value of at least 1.3V and a minimum value of at least −0.7V, the second voltage could have a value of no more than 0.1V, and the second voltage could be applied at five or more frequencies between 1 Hz and 100 kHz inclusive.

In a second embodiment, a system includes a sensor probe configured to receive a material being examined. The sensor probe includes a first electrode and a second electrode. The system also includes a sensor controller configured to measure a first current and to measure a second current. The first current is based on a varying first voltage provided across the electrodes during cyclic voltammetry measurements. The second current is based on a second voltage provided across the electrodes during impedance measurements. The sensor controller is also configured to identify a scaling factor using measurements of the second current, where the scaling factor is associated with an effective surface area of the electrodes. The sensor controller is further configured to identify a composition of the material being examined using measurements of the first current and the scaling factor.

In a third embodiment, an apparatus includes an electrode controller configured to provide voltages across electrodes of a sensor probe. The apparatus also includes a current monitor configured to measure currents flowing through at least one of the electrodes. The apparatus further includes a processor configured to receive measurements of a first current and measurements of a second current. The first current is based on a varying first voltage provided across the electrodes of the sensor probe during cyclic voltammetry measurements. The second current is based on a second voltage provided across the electrodes of the sensor probe during impedance measurements. The processor is also configured to identify a scaling factor using measurements of the second current, where the scaling factor is based on a capacitance associated with the electrodes. The apparatus is configured to identify a composition of a material being examined using measurements of the first current and the scaling factor.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawings, in which.

DETAILED DESCRIPTION

FIGS. 1 through 4, discussed below, and the various embodiments used to describe the principles of the present invention in this patent document are by way of illustration only and should not be construed in any way to limit the scope of the invention. Those skilled in the art will understand that the principles of the invention may be implemented in any type of suitably arranged device or system.

Figure 1:
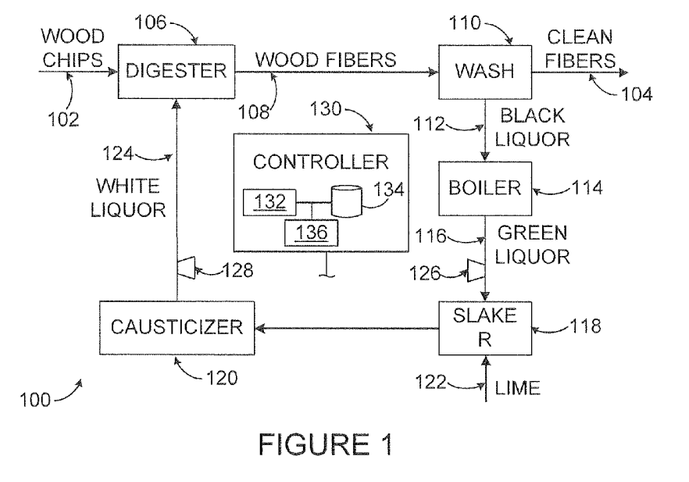
FIG. 1 illustrates an example wood pulping system according to this disclosure.

FIG. 1 illustrates an example wood pulping system 100 according to this disclosure. The embodiment of the wood pulping system 100 shown in FIG. 1 is for illustration only. Other embodiments of the wood pulping system 100 could be used without departing from the scope of this disclosure.

As shown in FIG. 1, the wood pulping system 100 receives wood chips 102 and operates to produce clean wood fibers 104. The wood chips 102 generally represent any suitable wood to be pulped. The wood chips 102 could also have any suitable size and shape suitable for pulping. The clean wood fibers 104 generally represent wood fibers from the wood chips 102 with undesirable components (such as lignin) removed. The clean wood fibers 104 can be provided to any suitable destination in any suitable form. As a particular example, the clean wood fibers 104 could be provided as pulp to a paper manufacturing system for use in forming large rolls of manufactured paper.

In this example, the wood pulping system 100 includes a digester 106. The digester 106 generally receives and digests the wood chips 102 to produce wood fibers 108. Here, the wood chips 102 are digested to dissolve the lignin that holds the wood fibers together. The digester 106 includes any suitable structure for digesting or dissolving wood chips. In particular embodiments, the digestion of the wood chips 102 in the digester 106 could occur using an alkaline solution that includes sodium hydroxide (NaOH) and sodium sulfide ($Na_2S$).

The wood fibers 108 are provided to a wash unit 110. The wash unit 110 washes or cleans the wood fibers 108 to produce the clean fibers 104. The wash unit 110 also produces a solution known as black liquor 112. During the wood pulping process, the hydroxide is consumed, and the sulfide is slowly converted into hydroxide. The black liquor 112 typically represents a mixture that includes the lignin dissolved from the wood chips 102 and any residual hydroxide and sulfide. The wash unit 110 includes any suitable structure for washing wood fibers.

The black liquor 112 is then processed in a boiler 114. For example, the black liquor 112 can be "burned" or boiled in the boiler 114. This produces a smelt that primarily includes sulfide and sodium carbonate ($Na_2CO_3$). The smelt is dissolved in water or "weak wash liquor" to produce green liquor 116. The boiler 114 includes any suitable structure for boiling material.

A slaker 118 and one or more causticizers 120 are used to convert the carbonate in the green liquor 116 into hydroxide, which can be recycled and reused in the pulping process. As shown here, the green liquor 116 reacts with lime 122 in the slaker 118, and the resulting material undergoes a causticizing reaction in the causticizers 120. This produces white liquor 124, which ideally contains a high degree of hydroxide and only a small amount of carbonate. The slaker 118 includes any suitable structure for reacting material with lime. The causticizers 120 include any suitable structure(s) for performing a causticizing reaction to convert carbonate into hydroxide.

The degree to which each step of the process occurs with maximum efficiency in FIG. 1 can greatly impact the purity of the white liquor 124, as well as the cost of the overall process. An inefficient causticizing reaction, for example, can result in relatively less hydroxide than ideal and more carbonate than ideal in the white liquor 124. The causticizing reaction is controlled by the amount of lime 122 introduced into the slaker 118 and the flow rate of green liquor 116 into the slaker 118. One or more of these variables (or other variables) can therefore be controlled to produce white liquor 124 having the appropriate or desired characteristics.

In order to accurately control the process performed in the wood pulping system 100, characteristics of the green liquor 116 and/or the white liquor 124 are measured and used to control the causticizing reaction. For example, the characteristics of the green liquor 116 or the white liquor 124 can be used to control the introduction of lime 122 into the slaker 118. U.S. Pat. No. 5,822,220 (which is hereby incorporated by reference) describes one example environment in which a causticizing reaction can be controlled.

To support the control of the system 100, one or more sensors 126-128 are used to measure one or more characteristics of the green liquor 116 and/or the white liquor 124. Measurement data from the sensors 126-128 can be provided to any suitable destination(s), such as a controller 130. The controller 130 could use the measurement data from the sensors 126-128 to control various components in the wood pulping system 100. The controller 130 could, for example, control the flow rates of green liquor 116 and lime 122 into the slaker 118 based on the measurement data from the sensors 126-128. In this way, the controller 130 could attempt to ensure that the white liquor 124 has desired characteristics.

As described in more detail below, each of the sensors 126-128 includes a probe with multiple electrodes. Also, the sensors 126-128 implement a technique called "cyclic voltammetry" or "sweeping voltammetry" to determine the concentration of various components in a material being examined (such as the green liquor 116 or the white liquor 124). In this technique, a varying or sweeping voltage is generated across electrodes in the sensor probe. This causes an oxidoreduction reaction to occur, which consumes or generates electrons and produces a current. The current is carried by ions in the material being examined and can be measured using the sensor probe. Current as a function of voltage (current versus voltage) and other data can then be collected by a sensor controller, which uses this data to determine concentrations of various components in the material being examined. This allows the sensor controller to identify the composition of the material being examined, such as the composition of the green liquor 116 and/or the white liquor 124. The identified composition(s) can then be provided to the controller 130, which adjusts the system 100 accordingly As noted above, the electrodes in the sensors 126-128 may suffer from contamination, scale, or other problems. These problems can interfere with the accuracy of the cyclic voltammetry measurements, thereby interfering with the control of the system 100.

In accordance with this disclosure, along with the cyclic voltammetry measurements, impedance measurements are also performed using the sensors 126-128. For example, a sinusoidal voltage of various frequencies can be applied across the electrodes on a sensor probe. The resulting current generated through the material being examined can be measured. The impedance measurements can allow the sensor controller to identify the conductivity of a material being examined, and the identified conductivity can be used to more accurately identify the composition of the material. Moreover, the impedance measurements can be used to identify a scaling factor. The scaling factor allows the current versus voltage data to be modified or adjusted based on an amount of contamination, scale, or other fouling affecting the electrodes of the sensor probe. In this way, the impedance measurements can be used to help ensure that more accurate current versus voltage data is used, even when contamination and scale alter the operation of the electrodes in the sensors 126-128.

Figure 2:
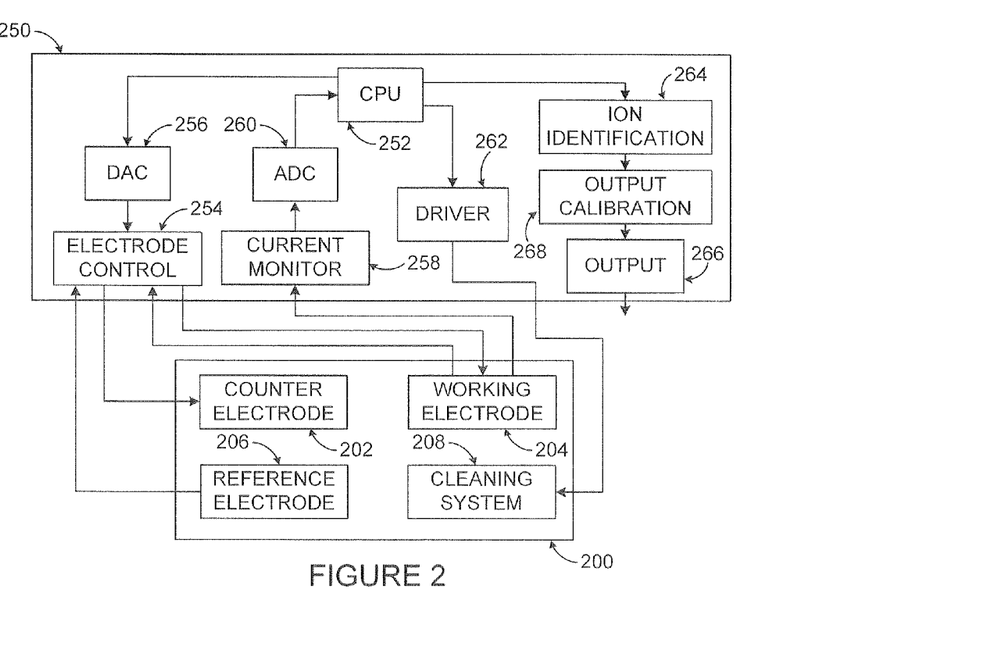
FIG. 2 illustrates an example sensor probe and an example sensor controller according to this disclosure.

Each of the sensors 126-128 includes any suitable structure(s) for taking cyclic voltammetry and impedance measurements of a material being examined, such as a probe and a controller. One example embodiment of a sensor is shown in FIG. 2, which is described below. Also, additional details regarding cyclic voltammetry measurements performed by a sensor (and additional details of an example sensor) can be found in U.S. Pat. No. 6,416,651 (which is hereby incorporated by reference).

The controller 130 includes any suitable structure for controlling one or more operations in the wood pulping system 100. The controller 130 could, for example, include at least one processor 132 and at least one memory 134 for storing instructions and data used, generated, or collected by the processor(s) 132. The controller 130 also includes at least one network interface 136 for communicating over a network, such as an Ethernet network or an electrical signal network facilitating communication between the controller 130 and the sensors 126-128.

Although FIG. 1 illustrates one example of a wood pulping system 100, various changes may be made to FIG. 1. For example, the system 100 has been simplified for ease of illustration and could include any other or additional components. Also, the system 100 could include any number of sensors and controllers, including a single sensor, more than two sensors, or more than one controller. In addition, FIG. 1 illustrates one operational environment in which impedance measurements can be used in conjunction with cyclic voltammetry measurements. This functionality could be used in any suitable device or system (whether or not that device or system relates to wood pulping) to measure any suitable material(s).

FIG. 2 illustrates an example sensor probe 200 and an example sensor controller 250 according to this disclosure. The embodiments of the sensor probe 200 and the sensor controller 250 shown in FIG. 2 are for illustration only. Other embodiments of the sensor probe 200 and/or the sensor controller 250 could be used without departing from the scope of this disclosure. Also, for ease of explanation, the sensor probe 200 and the sensor controller 250 are described as forming each of the sensors 126-128 in the wood pulping system 100 of FIG. 1. The sensor probe 200 and the sensor controller 250 could be used in any other suitable system.

In this example, the sensor probe 200 includes at least two electrodes 202-204. A voltage can be created across a counter electrode 202 and a working electrode 204. This creates a current due to an electrochemical reaction with a material being examined, and the working electrode 204 collects the current generated by that voltage and provides the current to the sensor controller 250. The sensor probe 200 may optionally include a reference electrode 206 and/or a cleaning system 208. The reference electrode 206 can be used to establish a base or zero potential point against which the other electrodes 202-204 can be measured (although the use of the reference electrode 206 is not required in the sensor probe 200). This may allow, for example, the voltage applied across the electrodes 202-204 during cyclic voltammetry measurements to be adjusted or controlled based on (i) the desired sweeping voltages and (ii) a voltage measured across the working electrode 204 and the reference electrode 206.

Each of the electrodes 202-206 includes any suitable structure for forming an electrical connection with a solution or other material being examined. Each of the electrodes 202-206 could also be formed from any suitable material(s), such as platinum, gold, carbon, graphite, iridium, palladium, stainless steel, or titanium. If the reference electrode 206 is included, it could be located as close as practical to the electrode(s) 202 or 204, and the three electrodes 202-206 could be mounted in the same plane. Although not shown, the working and reference electrodes 204-206 could be located symmetrically with respect to the counter electrode 202. This may allow the working and reference electrodes 204-206 to be swapped without affecting the sensor's calibration and output. Swapping of the working and reference electrodes 204-206 can help to prolong the life of the probe 200 (since the working electrode 204 can erode over time). The cleaning unit 208 generally represents any suitable structure for cleaning one or more of the electrodes to help maintain sensor accuracy and reduce electrode contamination. The cleaning unit 208 could, for example, represent an ultrasonic, mechanical, chemical, or other type of cleaning system.

As shown in FIG. 2, the sensor controller 250 includes a central processing unit (CPU) 252. The central processing unit 252 generally controls the overall operation of the sensor controller 250. The central processing unit 252 could, for example, control the voltages provided across the electrodes 202-204 in the sensor probe 200. The central processing unit 252 could also collect and analyze data associated with currents flowing through the electrode 204 in the sensor probe 200. In this way, the central processing unit 252 could collect information related to cyclic voltammetry measurements. The central processing unit 252 could also initiate impedance measurements involving the sensor probe 200. The resulting information could be collected and used by the central processing unit 252 to facilitate identification of the composition of a material being examined. The central processing unit 252 includes any suitable processing or control device. The central processing unit 252 could, for example, represent one or more microprocessors, microcontrollers, or other logic units.

An electrode controller 254 is coupled to the central processing unit 252 (possibly through a digital-to-analog converter 256). The electrode controller 254 provides voltages across the electrodes 202-204 in the sensor probe 200. The electrode controller 254 could, for example, receive excitation control signals from the central processing unit 252, where the excitation control signals control the voltages supplied across the electrodes 202-204. The electrode controller 254 includes any suitable structure for driving a voltage across electrodes. As noted above, voltages measured across the working electrode 204 and the reference electrode 206 could be used to adjust the voltages provided by the electrode controller 254 during cyclic voltammetry measurements. The digital-to-analog converter 256 includes any suitable structure for converting digital signals to analog signals.

A current monitor 258 is also coupled to the central processing unit 252 (possibly through an analog-to-digital converter 260). The current monitor 258 monitors or measures current flowing through the electrode 204 in the sensor probe 200 (such as current generated by applying a voltage across the electrodes 202-204). Current measurement values are then provided to the central processing unit 252 for use in identifying the composition of the material being examined. The current monitor 258 includes any suitable structure for measuring a current. The analog-to-digital converter 260 includes any suitable structure for converting analog signals to digital signals.

If some form of cleaning system 208 is available (either within or separate from the sensor probe 200), the central processing unit 252 could control the cleaning system 208 through a cleaning system driver 262. The cleaning system driver 262 can activate and control the operation of the cleaning system 208. The central processing unit 252 could, for example, periodically initiate a cleaning cycle by triggering electrically actuated relays in the cleaning system driver 262, which sends power to the cleaning system 208. The need and frequency for cleaning can depend on various factors, such as electrode composition, how quickly material being examined fouls the electrodes, and other factors. During cleaning, the central processing unit 252 can stop initiating measurements by the sensor probe 200 or ignore any measurements taken by the sensor probe 200, which can help to prevent use of erroneous data generated during a cleaning cycle.

An ion identification unit 264 receives data generated or collected by the central processing unit 252. The ion identification unit 264 also determines ion concentrations of components in the material being examined based on that data. For example, the ion identification unit 264 could receive current measurements and current gradients (derivatives) and determine the ion concentrations of sodium hydroxide, sodium carbonate, and sodium sulfide in the green liquor 116 and/or the white liquor 124. The ion identification unit 264 includes any suitable structure for identifying a composition of a material being examined based on voltage and current data.

The composition determined by the ion identification unit 264 can be provided to an output 266, which provides the composition or other signals to one or more control or other devices (such as the controller 130). The outputs could be in any suitable form, such as 4-20 mA or other analog signals. Control devices could use the signals, for example, to perform control operations related to the system 100. Control or other devices could also store or display the composition of the material being examined. As a particular example, signals from the output 266 could be provided to a control system for making changes to the rate at which lime 122 is added to the slaker 118 or for making changes to the operation of the causticizers 120. Some form of output calibration unit 268 may be included between the ion identification unit 264 and the output 266. The output calibration unit 268 could, for example, be used to adjust output values based on periodic, continuous, or initial calibration data.

It may be noted that while various components are shown in the sensor controller 250 of FIG. 2, various ones of these components may actually be implemented in software or firmware instead of using physical circuits. Also, various components in FIG. 2 could be combined or further subdivided, such as when the ion identification unit 264 is implemented as software that is executed by the central processing unit 252.

In one aspect of operation, the sensor probe 200 and the sensor controller 250 shown in FIG. 2 support the use of cyclic voltammetry. This involves providing a varying or sweeping voltage across the electrodes 202-204, where the voltage sweeps (changes) over one or more specified voltage ranges. This also involves measuring currents through the electrode 204. For certain chemical components in a solution or other material being examined, there is a given voltage range over which the current flowing between the electrodes 202-204 of the sensor probe 200 varies from:

(1) a small level that is essentially independent of the voltage applied to the material being examined;

(2) an intermediary quasi-stable level that varies with the content of the component of interest in the material being examined; and (3) a very high level that again is essentially independent of the voltage applied to the material being examined.

In other words, each component of the material being examined has a range of voltages in which it is possible to estimate the quantity of that component in the material. By sweeping a voltage across those ranges of interest, the sensor controller 250 can identify whether certain components are present in the material being examined and, if so, in what quantities they are present.

A voltammetric measurement for a given component in the material being examined involves obtaining repeated measurements of current-voltage points for voltages within the range associated with that particular component. Also, the ratio of the change in current against the change in voltage (dI/dv) in and around the half-wave potential can be measured for that particular component. The half-wave potential is the point where the current is mid-way between the lower level (independent of voltage) and the upper plateau (independent of voltage). It is also the point on the current-voltage curve where the slope is most vertical (again independent of voltage). This data can be used to estimate the ion concentration of that particular component in the material being examined. For instance, the ion identification unit 264 could compare a voltammetric-current curve for the specified component to a similar curve for a material having a known content of the component. The comparison typically provides some information about the content of the specific component in the material being examined. Additional details regarding cyclic voltammetry measurements can be found in U.S. Pat. No. 6,416,651, which has been incorporated by reference.

The sensor probe 200 and the sensor controller 250 shown in FIG. 2 also support additional impedance measurements that can be used to adjust or improve the cyclic voltammetry measurements. For example, the impedance measurements could involve applying low voltage sinusoidal signals at various frequencies across the electrodes 202-204. As a particular example, a sinusoidal voltage of 0.1V could be applied at five or more frequencies between 1 Hz and 100 kHz (inclusive), such as 5 Hz, 20 Hz, 100 Hz, 200 Hz, and 1 KHz. The low voltage is typically not near the reaction potential of the components of interest in the material being examined, so the impedance measurement is only significantly affected by the material's conductivity and the capacitance of the sensor's electrodes. As a result, the conductivity of the material being examined can be determined and used to determine the composition of the material.

Moreover, changes in the capacitance of the electrodes 202-204 in the sensor probe 200 can be determined using the impedance measurements. The increase in contaminants, scale, or other fouling of the electrodes 202-204 reduces the effective surface area of the electrodes. This typically results in a decay of the currents created during the cyclic voltammetry measurements. To compensate for this, based on the impedance measurements, the sensor controller 250 can generate a scaling factor that generally corresponds to a measure of the effective surface area of the electrodes 202-204. The scaling factor can then be used to adjust the data used by the sensor controller 250 to determine the composition of the material being examined. This may help to increase the accuracy of the sensor controller 250. Additional details regarding the analysis of the voltages and currents and the identification of a material's composition are provided in FIG. 3, which is described below.

In particular embodiments, the electrodes 204-206 can be swapped periodically or at other times. This swapping of electrode function could be done for one or several reasons, such as to ensure degradation of both the working and reference electrodes 204-206 and to increase the life of the sensor probe 200.

Although FIG. 2 illustrates one example of a sensor probe 200 and one example of a controller 250, various changes may be made to FIG. 2. For example, various components in FIG. 2 could be omitted, combined, or further subdivided and additional components could be added according to particular needs. Also, the sensor probe 200 could be incorporated into the sensor controller 250 or placed at any location accessible to the sensor controller 250.

Figure 3:
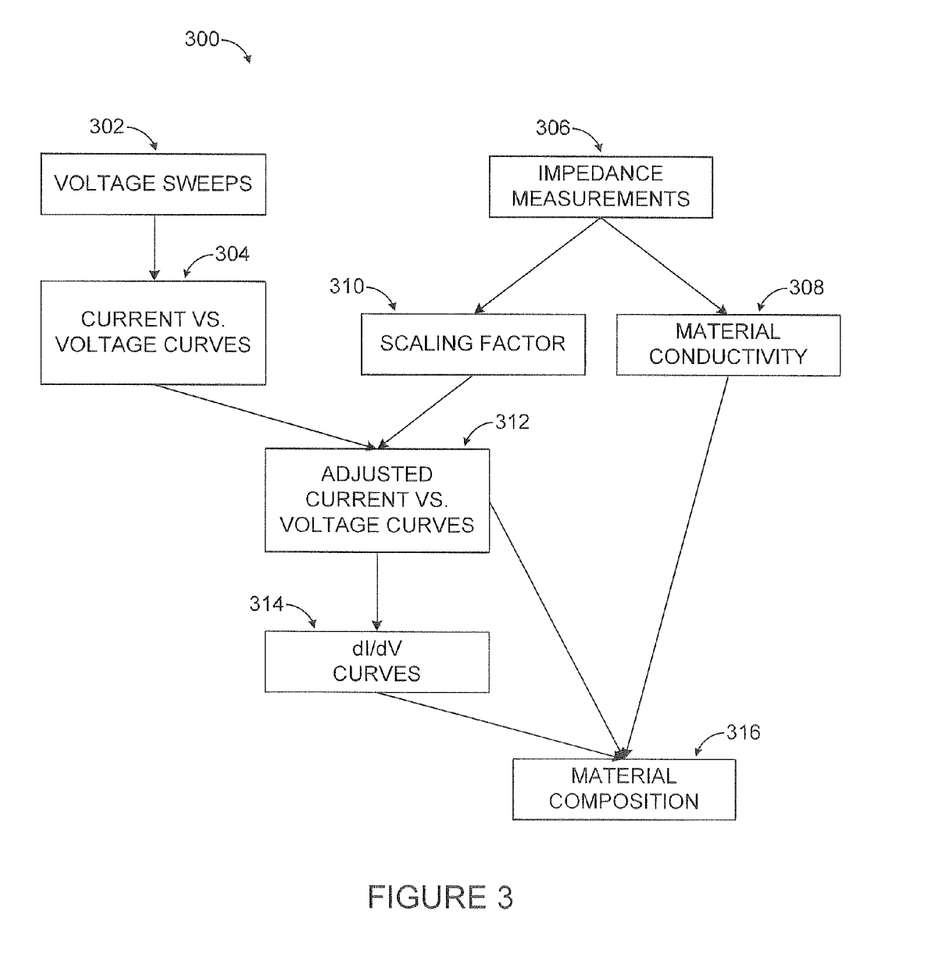
FIG. 3 illustrates an example composition determination process according to this disclosure.

FIG. 3 illustrates an example composition determination process 300 according to this disclosure. The embodiment of the composition determination process 300 shown in FIG. 3 is for illustration only. Other embodiments of the composition determination process 300 could be used without departing from the scope of this disclosure. Also, for ease of explanation, the composition determination process 300 is described with respect to the sensor probe 200 and sensor controller 250 shown in FIG. 2. The composition determination process 300 could be used by any suitable device(s) and in any suitable system.

Voltage sweeps 302 occur using the electrodes 202-206 in the sensor probe 200. For example, the central processing unit 252 could provide varying values to the digital-to-analog converter 256, which provides varying analog values to the electrode controller 254. This causes the electrode controller 254 to create a varying voltage across the electrodes 202-204. The voltage could be varied over one or several ranges, such as ranges around the half-wave potential of the ions to be measured (such as sodium hydroxide, sodium carbonate, and sodium sulfide). As particular examples, the voltage sweeps could occur between 0V and 1.3V or between −1.3V and 2.5V (Inclusive). As another particular example, a sweep voltage could be a triangular wave that goes from 0V up to 1.3V, then down to −0.7V and back to 0V. The range and characteristics of the voltage sweep (such as its speed and the shape of its voltage waveform) can also be adjusted based on several criteria, such as changes in liquid conductivity, composition, temperature, or other process parameters and previously collected data or empirically identified or calculated measurement locations.

During a voltage sweep 302, a current is created through the electrode 204 in the sensor probe 200, and the current is measured by the current monitor 258. The current measurements can be digitized, and the central processing unit 252 can generate current versus voltage curves 304. The curves 304 generally include various points that relate the voltages being applied during the voltage sweeps 302 and the current measurements associated with those voltages. This process could be repeated over several cycles (such as ten-second cycles) to collect data during multiple sweeps.

In between the voltage sweeps 302, impedance measurements 306 can occur. The impedance measurements 306 can involve the central processing unit 252 providing values to the digital-to-analog converter 256, which provides analog values to the electrode controller 254 that cause the electrode controller 254 to create low voltage sinusoidal signals across the electrodes 202-204. This also causes small currents to flow through the electrode 204, which are measured by the current monitor 258. The measured currents produced during an impedance measurement 306 can be used to identify the conductivity 308 of the material being examined.

The measured currents produced during the impedance measurements 306 can also be used to identify a scaling factor 310. As noted above, the scaling factor 310 can correspond to a measure of the effective surface area of the electrodes 202-204 in the sensor probe 200. In some embodiments, the scaling factor 310 is determined by fitting impedance versus frequency measurements to an impedance curve associated with known build-up of contaminants or other fouling of the electrodes 202-204.

Using the scaling factor 310, the current versus voltage curves 304 can be normalized or otherwise processed to produce adjusted current versus voltage curves 312. The adjusted curves 310 may represent a more accurate representation of the voltages and currents associated with the voltage sweeps 302 since the scaling factor 310 corrects for problems caused by contaminants or other fouling of the sensor electrodes 202-204. The adjusted curves 312 can then be further processed, such as by the central processing unit 252, to produce dI/dV curves 314. The dI/dV curves 314 generally denote the derivative of the current intensity or ratio of the change in current to the change in voltage. However, the dI/dV curves 314 are based on the adjusted curves 312. As a result, the dI/dV curves 314 may be more accurate because the effects caused by fouling of the sensor electrodes 202-204 have been reduced or eliminated using the scaling factor 310.

The material conductivity 308, the adjusted current versus voltage curves 312, and the dI/dV curves 314 can be used to determine a composition 316 of a solution or other material being examined. This could occur, for example, when the central processing unit 252 sends the appropriate data to the ion identification unit 264. The composition 316 could be determined using the conductivity 308, the adjusted current versus voltage curves 312, and the dI/dV curves 314. The composition 316 could also be determined using the adjusted current versus voltage curves 312 and the dI/dV curves 314 (and the determination of the conductivity 308 could be omitted from the process). In particular embodiments, whether the use of conductivity 308 can be omitted may depend on the composition of the material and whether all of the components have an electro-chemical signature.

The ion identification unit 264 can perform any suitable operations to identify the composition 316 of the material being examined. For example, the ion identification unit 264 could operate to identify points in the dI/dV waveform where increased ionic activity occurs. As a particular example, the ion identification unit 264 could search through the dI/dV waveform and identify the locations where the dI/dV ratio changes dramatically. As noted above, the approximate locations of these reactions of interest may already be known (since the half-wave potentials are well documented for various ions). By defining the search area to cover only the normal potential ranges of the ions of interest, the ion identification unit 264 can selectively detect any ion in the material being examined.

At each point where an ion is identified, the rate of current change can be recorded, as well as other information (such as the amount of current flow and the voltage at which the ion's reaction was located). This information could then be used to identify a composition of the material being examined. For example, this information could be applied to a linear equation obtained through an initial calibration or other mechanism. Several calibrations could be generated and stored concurrently, allowing the concentration of several different components in the material to be measured.

Various calibration options are available for correlating data to actual component concentration values. For example, it is possible to calculate concentrations based on known properties of ions and the measured currents associated with those ions.

As another example, linear regression and laboratory material samples having known component concentrations can be used to produce a set of calibration coefficients. In a simple case, dI/dv or a combination of dI/dv and current I at a particular voltage is associated with a particular concentration. In this type of technique, conductivity caused by ions measured at lower voltages can be subtracted from the measurement prior to producing a result (which is possible since a voltage sweep shows how each ion contributes to overall conductivity). Other factors can also be considered, such as temperature, material pH, or derivative values at other voltages (like at the half-wave potential of other ions). In this approach, a series of equations may be created, such as:

$$S_1(1)X_1+S_2(1)X_2+S_m(1)X_m+\ldots+X_0=L(1)$$

$$S_1(2)X_1+S_2(2)X_2+S_m(2)X_m+\ldots+X_0=L(2)$$

$$S_1(n)X_1+S_2(n)X_2+S_m(n)X_m+\ldots+X_0=L(n)$$

$$S_1(N)X_1+S_2(N)X_2+S_m(N)X_m+\ldots+X_0=L(N).$$

In the above equations, L(n) represents laboratory-analyzed material sample values (the actual values for the desired measured parameters at the given time). Also, $S_1(1) \ldots S_m(N)$ represent various sensor signals, such as one or more current derivatives, one or more current values, associated electrode voltages, material conductivity 308, impedance values, probe temperatures, or other measured parameters (like measurements from various field instruments, which could relate to any other measured parameters related to the composition determination). The value n represents the selected functions at a specific time. The set of equations chosen may represent all possible equations with the selected set of output signals or a subset of these equations (which could be based on a designer's understanding of more critical signals). The offset $X_0$ and the weights $X_1$-$X_m$ can be solved using matrix algebra, linear regression, or other suitable technique. A "sum of squares" approach can be used to minimize the sum of error through all equations.

Since there may be no set of coefficients that exactly fits all equations simultaneously, a coefficient of correlation R can be output, which represents how well a linear model fits the test data. The value of R can be calculated as the ratio of standard deviations of the laboratory data and the calculated data, where 1.0 means that all variation in laboratory data can be explained by the variations in the measured signals and 0.0 means that there is no relationship between the laboratory data and measured signals. The coefficient of correlation can be used to select which parameters, of the ones chosen, provide the most accurate representation of the system. Of course, other correlation methods could also be used. Once calibration is completed, a real-time output O can be generated, such as by using the output calculation formula:

$$O=X_0+S_1X_1+S_2X_2+S_3X_3+\ldots+S_nX_n$$

Here, $S_1$-$S_n$ represent selected sensor signals as defined above, $X_0$ is an offset, and $X_1$-$X_m$ are weight coefficients obtained during calibration.

In the example shown in FIG. 3, it can be seen that the scaling factor 310 allows alteration of the information used to generate the dI/dV curves 314. In particular, the scaling factor 310 allows the current versus voltage curves 304 to be adjusted based on contamination, scaling, or other fouling of the sensor electrodes 202-204. As a result, the cyclic voltammetry measurements may be accurate even as fouling of the sensor electrodes 202-204 occurs over time. This may allow more effective control of a system to occur based on the cyclic voltammetry measurements.

It may be noted that the scaling factor 310 here represents the effect of contamination, scaling, or other fouling of the counter and working electrodes 202-204. If the counter electrode 202 is significantly larger than the working electrode 204, the scaling factor 310 could represent the effect of fouling of the working electrode 204 only, and a second scaling factor could be obtained to account for fouling of the reference electrode 206. This could be done using impedance measurements and by swapping the working and reference electrode functions. It may also be noted that fouling of the reference electrode 206 may not affect the cyclic voltammetry measurements as much as fouling of the working electrode 204 since the reference electrode 206 is merely used as a potential reference.

Although FIG. 3 illustrates one example of a composition determination process 300, various changes may be made to FIG. 3. For example, the composition of the material being examined could be identified based on the adjusted current versus voltage curves 312 without requiring use of the dI/dV curves 314.

Figure 4:
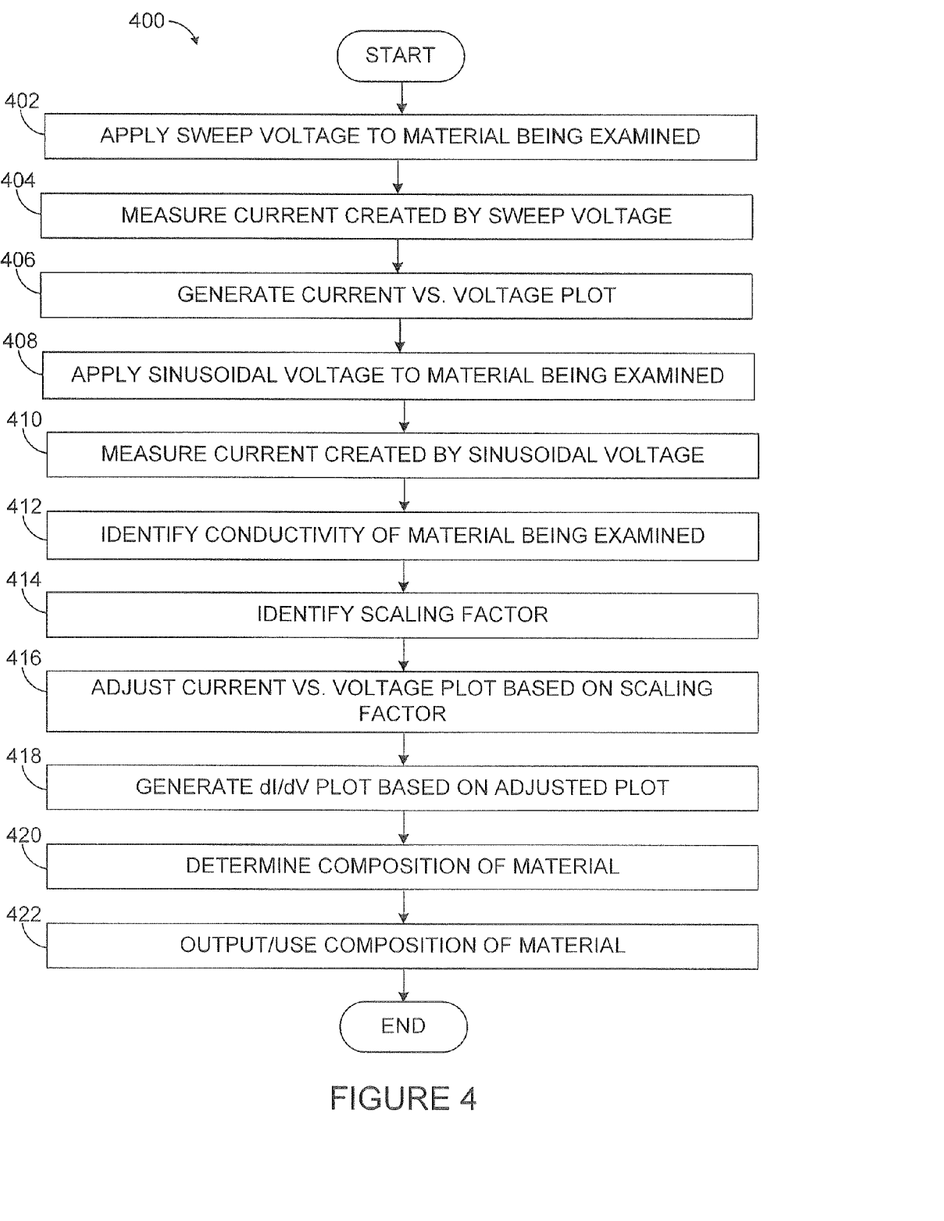
FIG. 4 illustrates an example method for determining a composition of a liquid material according to this disclosure.

FIG. 4 illustrates an example method 400 for determining a composition of a liquid material according to this disclosure. The embodiment of the method 400 shown in FIG. 4 is for illustration only. Other embodiments of the method 400 could be used without departing from the scope of this disclosure. Also, for ease of explanation, the method 400 is described with respect to the sensor probe 200 and controller 250 shown in FIG. 2. The method 400 could be used by any suitable device(s) and in any suitable system.

A sweep voltage is applied to a material being examined at step 402. This could include, for example, a sensor applying a voltage that is swept over one or more ranges of interest across the electrodes 202-204 of a sensor probe 200. A current created by the sweep voltage is measured at step 404. This could include, for example, the current monitor 258 measuring the current flowing through the electrode 204 of the sensor probe 200. A current versus voltage plot is generated at step 406. This could include, for example, the central processing unit 252 generating a current-voltage curve based on multiple measured current-voltage points. The current-voltage plot generally defines how the measured current varied with the sweep voltage.

A sinusoidal voltage is also applied to the material being examined at step 408, and a current created by the sinusoidal voltage is measured at step 410. This could include, for example, the sensor applying a small voltage across the electrodes 202-204. The small voltage could be 0.1V and can be applied at multiple frequencies (such as five or more between 1 Hz and 100 kHz). This could also include the current monitor 258 measuring the current flowing through the electrode 204 of the sensor probe 200.

The conductivity of the material being examined is determined at step 410. This could include, for example, the sensor controller 250 determining the conductivity based on the measured currents generated using the sinusoidal voltage at different frequencies.

A scaling factor is also determined at step 412. The scaling factor could, for example, represent a measure of the effective surface area of the electrodes 202-204 in the sensor probe 200. The scaling factor could be produced in any suitable manner. For example, the scaling factor could be determined by fitting a measured impedance versus frequency curve to impedances associated with known build-up of contaminants or other fouling of the electrodes 202-204.

The generated current-voltage plot is then adjusted using the scaling factor at step 416. This could include, for example, normalizing the current values in the plot based on the identified scaling factor. The adjusted current-voltage plot can then be used to generate a dI/dV plot at step 418. The dI/dV plot represents the current derivative in the adjusted current-voltage plot. The dI/dV plot generated here may be less susceptible to problems with the sensor electrodes since the effects of electrode fouling have been reduced or eliminated using the scaling factor.

The composition of the material being examined is determined at step 420. This could include, for example, the ion identification unit 264 identifying locations in the dI/dV plot where the current derivative changes dramatically. These areas can be examined to estimate the content of particular components in the material based on the measured currents. This could also include using the determined conductivity of the material.

The identified composition of the material could then be output or used in any suitable manner. For example, the identified composition could be stored in a memory or displayed to a user. The identified composition could also be provided to a process controller (such as the controller 130). The process controller 130 could then make adjustments to a process being controlled.

Although FIG. 4 illustrates one example of a method 400 for determining a composition of a liquid material, various changes may be made to FIG. 4. For example, the composition of the material being examined could be identified without requiring use of a dI/dV plot. Also, while shown as a series of steps, various steps in FIG. 4 could overlap, occur in parallel, occur in a different order, or occur multiple times.

In some embodiments, various functions described above are implemented or supported by a computer program that is formed from computer readable program code and that is embodied in a computer readable medium. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory.

It may be advantageous to set forth definitions of certain words and phrases used throughout this patent document. The term "couple" and its derivatives refer to any direct or indirect communication between two or more elements, whether or not those elements are in physical contact with one another. The terms "application" and "program" refer to one or more computer programs, software components, sets of instructions, procedures, functions, objects, classes, instances, related data, or a portion thereof adapted for implementation in a suitable computer code (including source code, object code, or executable code). The terms "transmit," "receive," and "communicate," as well as derivatives thereof, encompass both direct and indirect communication. The terms "include" and "comprise," as well as derivatives thereof, mean inclusion without limitation. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like. The term "controller" means any device, system, or part thereof that controls at least one operation. A controller may be implemented in hardware, firmware, software, or some combination of at least two of the same. The functionality associated with any particular controller may be centralized or distributed, whether locally or remotely.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A method comprising:
    identifying first data associated with cyclic voltammetry measurements of a material being examined, the cyclic voltammetry measurements comprising applying a varying first voltage across first and second electrodes of a sensor probe configured to receive the material and measuring a first current generated using the varying first voltage;
    identifying second data associated with impedance measurements, the impedance measurements comprising applying a second voltage across the first and second electrodes and measuring a second current generated using the second voltage, the second data comprising a scaling factor associated with an effective surface area of the electrodes;
    adjusting at least part of the first data using the scaling factor; and
    identifying at a sensor controller a composition of the material using the adjusted first data.

2. The method of claim 1, wherein:
    identifying the second data comprises identifying a conductivity of the material being examined; and
    identifying the composition of the material comprises using the identified conductivity of the material.

3. The method of claim 1, wherein:
    the cyclic voltammetry measurements comprise applying the first voltage across the first and second electrodes of the sensor probe during multiple cycles; and
    further comprising swapping the second electrode and a third electrode during the multiple cycles of the cyclic voltammetry measurements.

4. The method of claim 1, wherein the second voltage is applied at multiple frequencies and has a magnitude substantially less than the varying first voltage.

5. The method of claim 4, wherein:
    the first voltage has a maximum value of at least 1.3V and a minimum value of at least −0.7V;
    the second voltage has a value of no more than 0.1V; and
    the second voltage is applied at five or more frequencies, the five or more frequencies between 1 Hz and 100 kHz inclusive.

6. The method of claim 1, wherein identifying the first data comprises:
    applying a sweep voltage that varies over a range of voltages to the material being examined;
    measuring the first current, the first current based on the sweep voltage; and
    generating a current versus voltage curve that associates values of the first current to values of the sweep voltage.

7. The method of claim 6, wherein identifying the second data comprises:
    applying a sinusoidal voltage at multiple frequencies to the material being examined;

measuring the second current, the second current based on the sinusoidal voltage; and generating the scaling factor using measurements of the second current.

8. The method of claim 7, wherein adjusting at least part of the first data comprises normalizing the current versus voltage curve using the scaling factor to produce a normalized current versus voltage curve.

9. The method of claim 8, further comprising:

generating a current derivative curve using the normalized current versus voltage curve, the current derivative curve associating changes in the first current against changes in the sweep voltage as identified in the normalized current versus voltage curve.

10. The method of claim 9, wherein identifying the composition of the material comprises using the current derivative curve.

11. A system comprising:

a sensor probe configured to receive a material being examined, the sensor probe comprising a first electrode and a second electrode; and a sensor controller programmed to:
measure a first current that is based on a varying first voltage provided across the electrodes during cyclic voltammetry measurements;
measure a second current that is based on a second voltage provided across the electrodes during impedance measurements;
identify a scaling factor using measurements of the second current, the scaling factor associated with an effective surface area of the electrodes; and
identify a composition of the material being examined using measurements of the first current and the scaling factor.

12. The system of claim 11, wherein:

the sensor controller is further programmed to identify a conductivity of the material being examined using the second current and the second voltage; and the sensor controller is programmed to identify the composition of the material using the identified conductivity of the material.

13. The system of claim 11, wherein:

the sensor controller is programmed to provide a sweep voltage across the electrodes as the varying first voltage, the sweep voltage varying over a range of voltages; and the sensor controller is further programmed to generate a current versus voltage curve that associates values of the first current to values of the sweep voltage.

14. The system of claim 13, wherein the sensor controller is programmed to identify the composition of the material by normalizing the current versus voltage curve using the scaling factor to produce a normalized current versus voltage curve.

15. The system of claim 14, wherein:

the sensor controller is programmed to identify the composition of the material further by generating a current derivative curve using the normalized current versus voltage curve; and the current derivative curve associates changes in the first current against changes in the sweep voltage as identified in the normalized current versus voltage curve.

16. An apparatus comprising:

an electrode controller programmed to provide voltages across electrodes of a sensor probe;

a current monitor configured to measure currents flowing through at least one of the electrodes; and logic stored in a computer readable medium and executable by a processor, the logic programmed to:
receive measurements of a first current, the first current based on a varying first voltage provided across the electrodes of the sensor probe during cyclic voltammetry measurements;
receive measurements of a second current, the second current based on a second voltage provided across the electrodes of the sensor probe during impedance measurements; and
identify a scaling factor using measurements of the second current, the scaling factor based on a capacitance associated with the electrodes;

wherein the apparatus is configured to identify a composition of a material being examined using measurements of the first current and the scaling factor.

17. The apparatus of claim 16, further comprising:

an ion identification unit configured to identify the composition of the material being examined.

18. The apparatus of claim 16, wherein:

the electrode controller is programmed to provide a sweep voltage across the electrodes as the first voltage, the sweep voltage varying over a range of voltages; and the logic is further programmed to generate a current versus voltage curve that associates values of the first current to values of the sweep voltage.

19. The apparatus of claim 18, wherein the logic is further programmed to normalize the current versus voltage curve using the scaling factor to produce a normalized current versus voltage curve.

20. The apparatus of claim 19, wherein:

the logic is further programmed to generate a current derivative curve using the normalized current versus voltage curve;

the current derivative curve associates changes in the first current against changes in the sweep voltage as identified in the normalized current versus voltage curve; and the current derivative curve is used to identify the composition of the material.

* * * * *